US010946822B2

(12) United States Patent
Gupta et al.

(10) Patent No.: US 10,946,822 B2
(45) Date of Patent: *Mar. 16, 2021

(54) VEHICLE FRAME COMPONENT

(71) Applicant: Ford Global Technologies, LLC, Dearborn, MI (US)

(72) Inventors: Ajay Kumar Gupta, Troy, MI (US); Narayana Venugopal, Northville, MI (US); John Charles Caris, Hartland, MI (US); Mark Wlotkowski, Royal Oak, MI (US); Charles Ko, Novi, MI (US); Leonard Anthony Shaner, New Baltimore, MI (US)

(73) Assignee: FORD GLOBAL TECHNOLOGIES, LLC, Dearborn, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/663,411

(22) Filed: Oct. 25, 2019

(65) Prior Publication Data
US 2020/0070759 A1 Mar. 5, 2020

Related U.S. Application Data

(62) Division of application No. 15/970,483, filed on May 3, 2018, now Pat. No. 10,501,035, which is a division
(Continued)

(51) Int. Cl.
*B60R 19/00* (2006.01)
*B62D 21/15* (2006.01)
(Continued)

(52) U.S. Cl.
CPC ............ *B60R 19/00* (2013.01); *A61M 25/02* (2013.01); *B60R 19/26* (2013.01); *B60R 21/00* (2013.01);
(Continued)

(58) Field of Classification Search
CPC .... B62D 21/15; B62D 21/152; B62D 21/155; B60R 19/00; B60R 19/02; B60R 19/026;
(Continued)

(56) References Cited

U.S. PATENT DOCUMENTS 2,639,186 A   5/1953   Sewelin
3,734,223 A   5/1973   Anderson
(Continued)

FOREIGN PATENT DOCUMENTS

DE            4227668 A1    2/1994
DE        102004021165 A1   11/2005
(Continued)

OTHER PUBLICATIONS

Screenshot—Mopar, p. 2011, www.moparpartswebstore.com/a/Dodge_2011_Ram-1500/66781587_5544376/Frame-Complete--1205-Inch-Wheel-Base/i2256058.html#1.
(Continued)

*Primary Examiner* — Dennis H Pedder
(74) *Attorney, Agent, or Firm* — Raymond L. Coppiellie; Bejin Bieneman PLC

(57) ABSTRACT

A vehicle frame component for limiting the movement of the wheel of the vehicle toward the cab of a cab on frame vehicle including a base member welded to openings in the frame side rail and extending outwardly and located proximal the wheel structure. In one embodiment the vehicle frame component is located forward of the wheel and includes a tire puncture device to deflate the tire during an offset front impact and in a second embodiment the vehicle frame component is located rearward of the wheel. The vehicle frame component has particular utility during an offset front impact where the offset is less than approximately twenty-five percent (25%) of the width of the vehicle.

19 Claims, 15 Drawing Sheets

Related U.S. Application Data of application No. 15/389,993, filed on Dec. 23, 2016, now Pat. No. 9,988,004, which is a division of application No. 14/926,140, filed on Oct. 29, 2015, now Pat. No. 9,566,922, which is a division of application No. 14/725,735, filed on May 29, 2015, now Pat. No. 9,376,073, which is a division of application No. 13/966,790, filed on Aug. 14, 2013, now Pat. No. 9,079,619.

(51) Int. Cl.

| | | |
|---|---|---|
| *B62D 25/08* | (2006.01) | |
| *B62D 27/02* | (2006.01) | |
| *B60R 21/00* | (2006.01) | |
| *B62D 21/09* | (2006.01) | |
| *A61M 25/02* | (2006.01) | |
| *B60R 19/26* | (2006.01) | |
| *B62D 29/00* | (2006.01) | |
| *B62D 33/077* | (2006.01) | |
| *B60R 19/02* | (2006.01) | |

(52) U.S. Cl.
CPC ........... *B62D 21/09* (2013.01); *B62D 21/152* (2013.01); *B62D 21/155* (2013.01); *B62D 21/157* (2013.01); *B62D 25/08* (2013.01); *B62D 25/082* (2013.01); *B62D 27/02* (2013.01); *B62D 27/023* (2013.01); *B62D 29/007* (2013.01); *B62D 33/077* (2013.01); *A61M 2025/0273* (2013.01); *B60R 19/02* (2013.01); *B60R 2019/002* (2013.01); *B60R 2019/026* (2013.01); *B60R 2021/0004* (2013.01); *B60R 2021/0023* (2013.01); *B60Y 2200/141* (2013.01); *B60Y 2200/142* (2013.01); *B60Y 2410/124* (2013.01)

(58) Field of Classification Search
CPC ...... B60R 2012/0004; B60R 2019/026; B60R 2021/0004
USPC .................. 296/187.09, 187.1, 35.1, 35.3
See application file for complete search history.

(56) References Cited

U.S. PATENT DOCUMENTS

| | | |
|---|---|---|
| 3,847,426 A | 11/1974 | McGettigan |
| 3,881,742 A | 5/1975 | Felzer |
| 4,819,980 A | 4/1989 | Sakata et al. |
| 5,033,522 A | 7/1991 | Metraux |
| 5,219,439 A | 6/1993 | Moore et al. |
| 5,275,436 A | 1/1994 | Pomero |
| 5,700,033 A | 12/1997 | Beckman |
| 5,967,597 A | 10/1999 | Vander Kooi et al. |
| 6,032,497 A | 3/2000 | Fulcher et al. |
| 6,364,358 B1 | 4/2002 | Miller |
| 6,460,889 B2 | 10/2002 | Iyanagi et al. |
| 6,511,119 B2 | 1/2003 | Takase et al. |
| 6,523,876 B1 | 2/2003 | Durand |
| 6,799,794 B2 | 10/2004 | Mochidome et al. |
| 6,854,553 B2 | 2/2005 | Sovoda et al. |
| 6,866,115 B2 | 3/2005 | Miyasaka |
| 7,163,259 B2 | 1/2007 | Hayashi |
| 7,201,398 B1 | 4/2007 | Christofaro et al. |
| 7,819,218 B2 | 10/2010 | Eichberger et al. |
| 7,926,847 B2 | 4/2011 | Auer et al. |
| 8,099,984 B2 | 1/2012 | Wu |
| 8,353,380 B2 | 1/2013 | Schonberger et al. |
| 8,544,589 B1 | 10/2013 | Rupp et al. |
| 8,807,597 B2 | 8/2014 | Akaki et al. |
| 8,915,530 B2 | 12/2014 | Wagner et al. |
| 9,079,619 B2 | 7/2015 | Gupta et al. |
| 10,501,035 B2 * | 12/2019 | Gupta .................. B62D 25/08 |
| 2006/0273606 A1 | 12/2006 | Rasmussen |
| 2008/0007096 A1 | 1/2008 | Fleming |
| 2009/0146462 A1 | 6/2009 | Sato et al. |
| 2010/0140965 A1 | 6/2010 | Schoenberger et al. |
| 2012/0025555 A1 | 2/2012 | Rasmussen |
| 2013/0081897 A1 | 4/2013 | Dandekar et al. |
| 2014/0062129 A1 | 3/2014 | Syed et al. |
| 2015/0084322 A1 | 3/2015 | Killian et al. |

FOREIGN PATENT DOCUMENTS

| | | |
|---|---|---|
| DE | 102010031089 A1 | 1/2012 |
| DE | 102011116448 A1 | 4/2013 |
| DE | 102012004682 A1 | 9/2013 |
| DE | 102012013277 A1 | 1/2014 |
| EP | 0921051 A2 | 6/1999 |
| EP | 1647456 A2 | 4/2006 |
| GB | 2482002 A | 1/2012 |
| NL | 1000632 C1 | 12/1996 |
| WO | 2007101285 A2 | 9/2007 |
| WO | 2012110529 A1 | 8/2012 |
| WO | 2013146495 A1 | 10/2013 |

OTHER PUBLICATIONS

Simmons, "A preliminary assessment of the risks associated with engine immobilisers", IEE Colloquium on Vehicle Security System, Oct. 8, 1993.

* cited by examiner

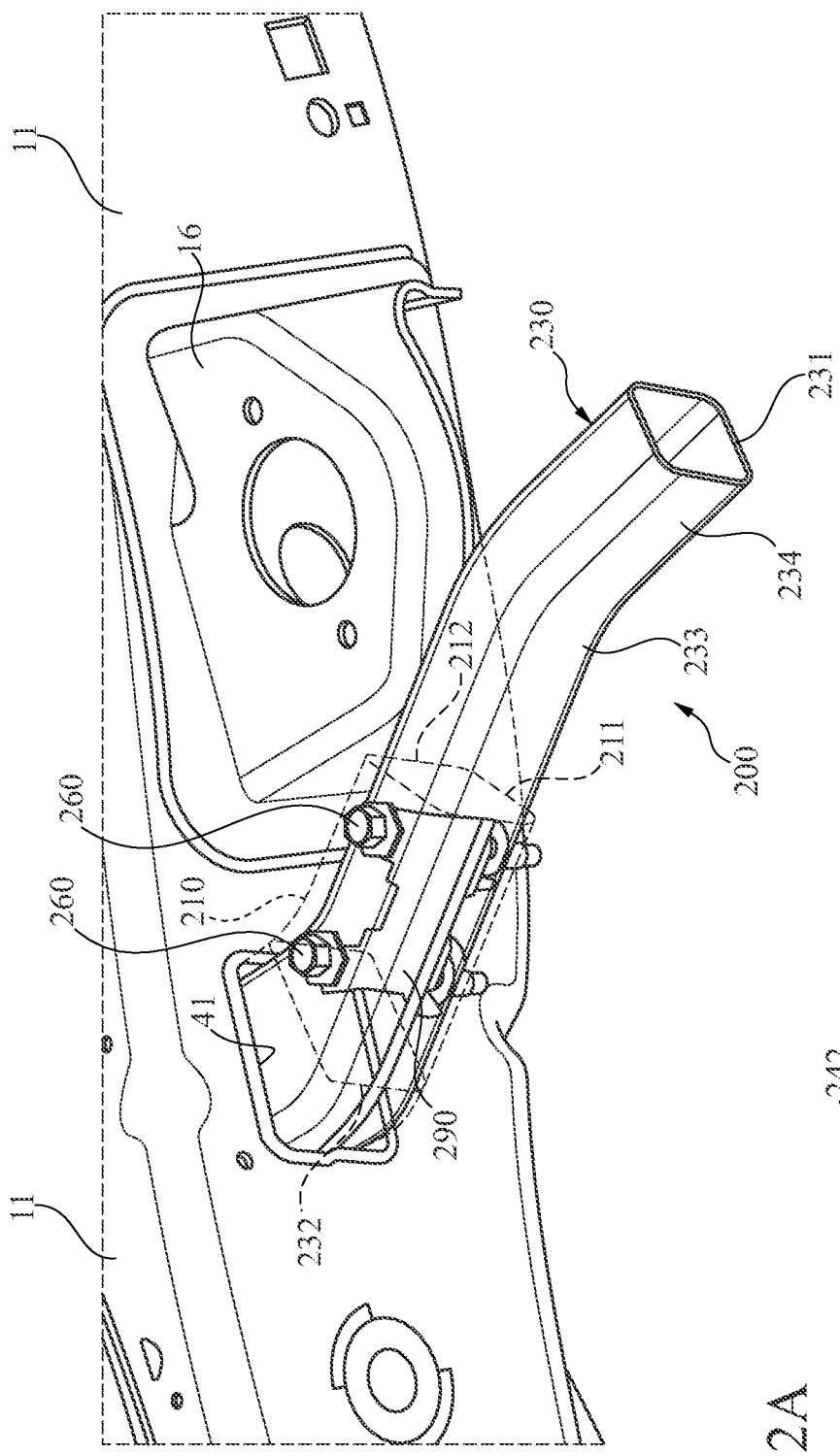
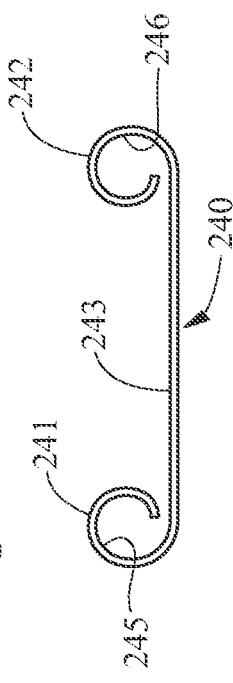
Fig. 12
Fig. 12A

VEHICLE FRAME COMPONENT

CROSS-SECTION TO RELATED APPLICATIONS

This patent application is a divisional of, and claims priority to and all advantages of, U.S. patent application Ser. No. 15/970,483 filed May 3, 2018, which is a divisional of, and claims priority to U.S. patent application Ser. No. 15/389,993 filed on Dec. 23, 2016, now issued as U.S. Pat. No. 9,988,004, which is a divisional of, and claims priority to U.S. patent application Ser. No. 14/926,140 filed on Oct. 29, 2015, now issued as U.S. Pat. No. 9,566,922, which is a divisional of, and claims priority to and all advantages of, U.S. patent application Ser. No. 14/725,735 filed on May 29, 2015, now issued as U.S. Pat. No. 9,376,073, which is a divisional of, and claims priority to and all advantages of, U.S. patent application Ser. No. 13/966,790 filed on Aug. 14, 2013, now issued as U.S. Pat. No. 9,079,619, each of which is incorporated herein in its entirety.

BACKGROUND

It is generally known to provide a vehicle including a vehicle frame. It is generally known to provide a cab on frame type vehicle where a cab or body is produced and then installed on the separately produced and shipped vehicle frame. It is generally known to provide a body on frame structure for use with a pickup type vehicle.

A small overlap frontal crash test is designed to replicate what happens when only a relatively small portion of the front corner of a vehicle collides with another object like a vehicle, tree, utility pole or the like. To test vehicles for this type of performance, a small overlap frontal test has been developed. In the small overlap frontal test, a vehicle travels at 40 mph toward a 5-foot-tall rigid barrier and only the outer 25% of the vehicle width is impacted into the barrier—see FIG. 1. It is generally understood that most modern vehicles are designed to have safety cages encapsulating the occupant compartment and built to withstand head-on and overlap frontal crashes with controlled and limited deformation. This is because the crush zones of the main body and frame structures are designed to manage the crash energy to reduce forces on the occupant compartment and its occupants. When a crash involves these structures, the occupant compartment is generally protected from intrusion, and the airbags and safety belts can perform to restrain and help protect occupants. Small overlap frontal crashes primarily affect a vehicle's outer edges, which may not be directly protected by the known crush-zone structures. Crash forces may go directly into the front wheel, suspension system and firewall. In a small overlap crash which does not engage the main structures of the vehicle it may be possible for the wheel to be forced rearward toward the occupant compartment. It is believed that the safety cage or cab needs to resist such crash forces that aren't tempered by crush-zone structures.

Even though such crush-zone and body (or cab) on frame type structures have long been known, there remains a continuing and significant need to provide added improved impact or crush performance. In particular, there long remains a continuing and significant need to provide additional improved impact performance by better reducing intrusion of the forward structures of the vehicle into the body or cab of the vehicle.

DRAWINGS

FIG. 12 is partial, graphic perspective view of the rear blocker structure of the exemplary embodiment of FIG. 3;

FIG. 12A is top plan graphic view of the clip support structure of the exemplary embodiment of FIG. 12;

DETAILED DESCRIPTION

Figure 2:
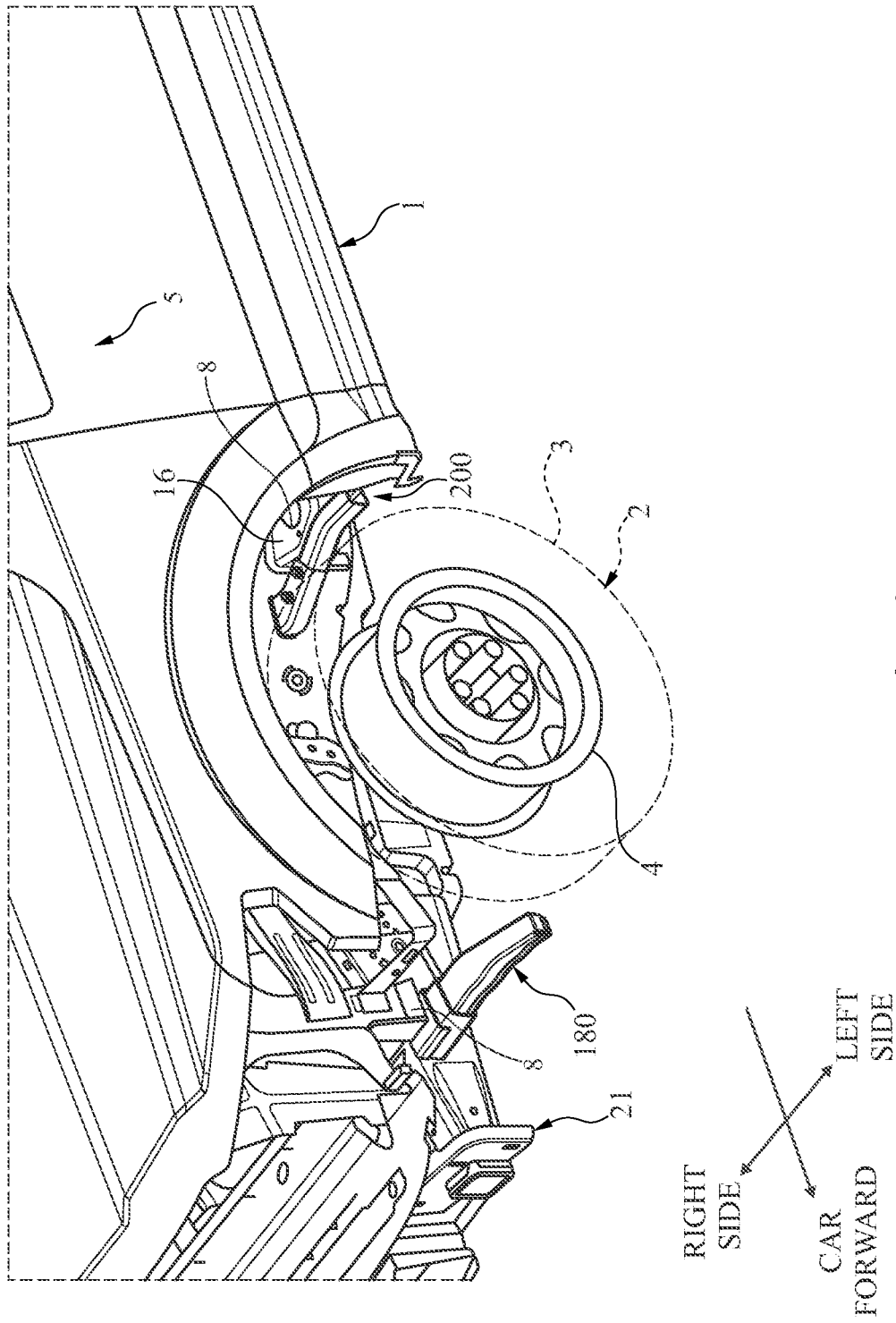
FIG. 2 is a partial, perspective graphic view of a vehicle including front and rear tire blocker structures according to an exemplary embodiment of the present disclosure.
Figure 3:
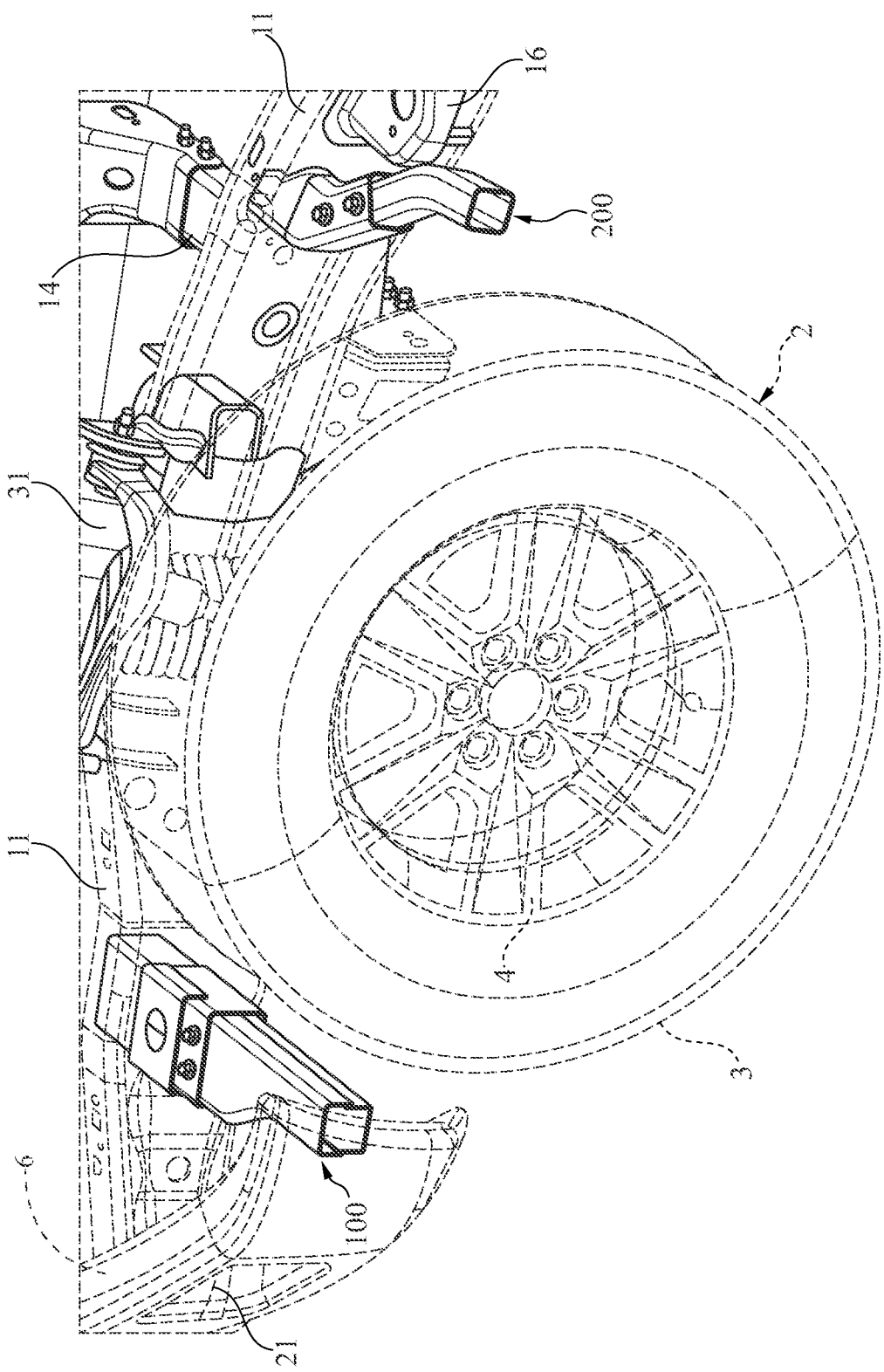
FIG. 3 is a perspective graphic view of front and rear tire blocker structures according to an exemplary embodiment of the present disclosure.

Referring in general to all of the Figures and in particular to FIGS. 3 through 10, there is disclosed in an exemplary embodiment of a portion of a vehicle 1. The vehicle 1 may include a wheel 2 for providing mobility to the vehicle 1. The wheel 2 may include a tire 3 and a rim 4. The vehicle 1 may include a vehicle frame 10 and a cab or body 7 as best shown in FIG. 2. Accordingly, the vehicle 1 has a cab (or body) on frame construction such as may be known for use as a pickup truck or the like. The vehicle 1 further includes a bumper or impact absorber 6 located at the car forward end of the vehicle 1. Referring now with a particular focus on FIG. 4, it may be observed that the vehicle frame 10 may include right side and left side and right-side side beams, frame rails or members 11 and 12, respectively, as may be generally known for a cab on frame type vehicle. It should be noted that the frame side rails 11 and 12 generally extend in a direction aligned with the car forward direction of vehicle 1 is identified by the directional arrows on the left side of FIGS. 2 and 4.

The vehicle frame 10 further includes a plurality of cross members for coupling the left and right side rails frame members 11 and 12, respectively. A first cross frame member 13 is located proximal the car forward direction and extends between the left-side frame rail 11 and the right-side frame rail 12. A second cross frame member 14 also extends between the left-side frame rail 11 in the right-side frame rail 12 at a location rearward of the cross frame member 13 and generally aligned with and proximal the wheels 2 of the vehicle 1. The vehicle frame 10 further includes a cross frame member 15 located rearward of the cross frame members 13 and 14 and generally aligned under a passenger compartment 5 of the cab 7 of the vehicle 1. The cross frame members 13, 14 and 15 extend longitudinally and the cross car direction and are coupled to the left-side frame rail 11 and the right-side frame rail 12 using any known or appropriate structure or process.

Figure 4:
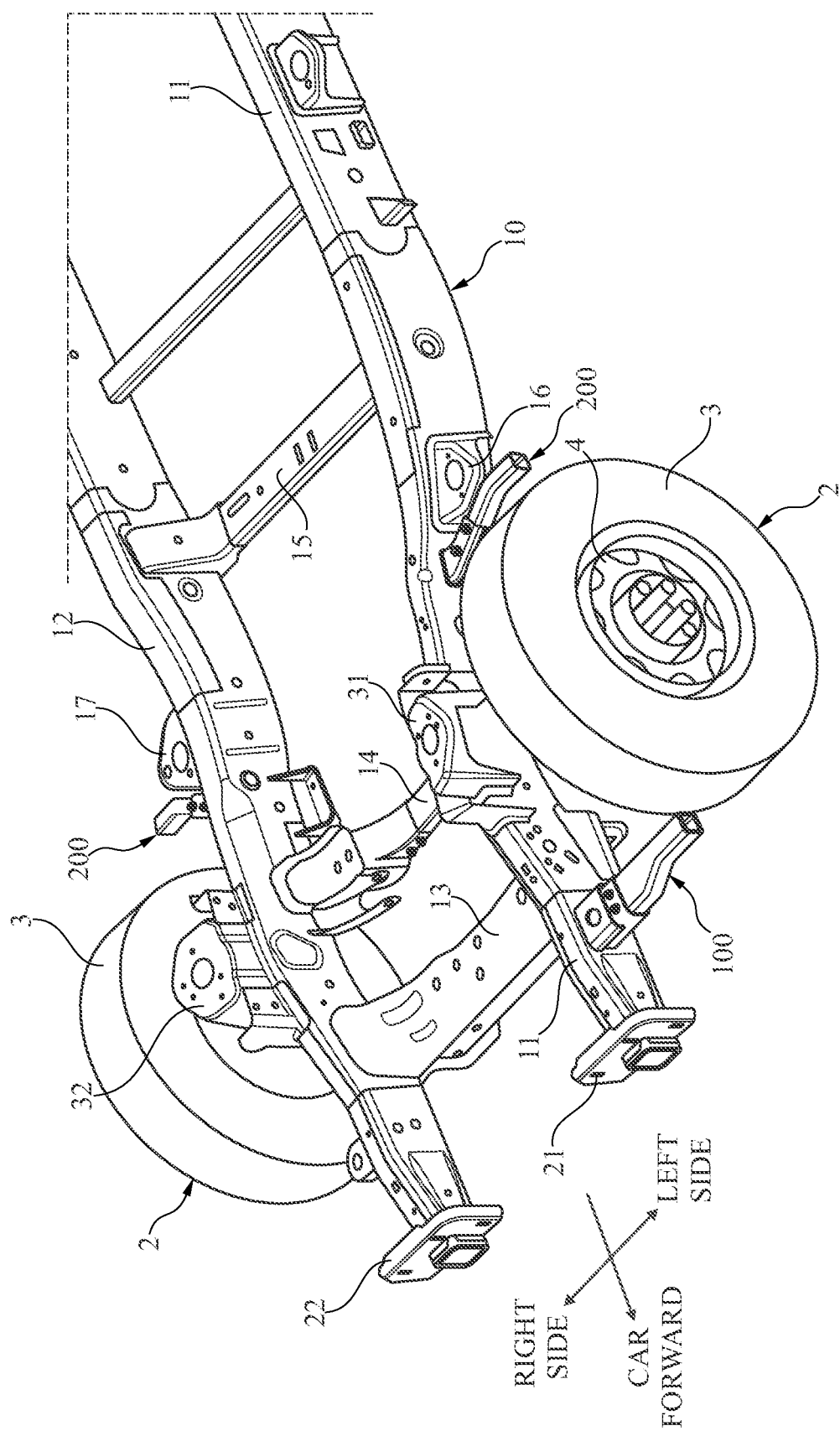
FIG. 4 is a partial, perspective graphic view of the exemplary embodiment of FIG. 3 with the vehicle cab structure removed and showing the frame.
Figure 5:
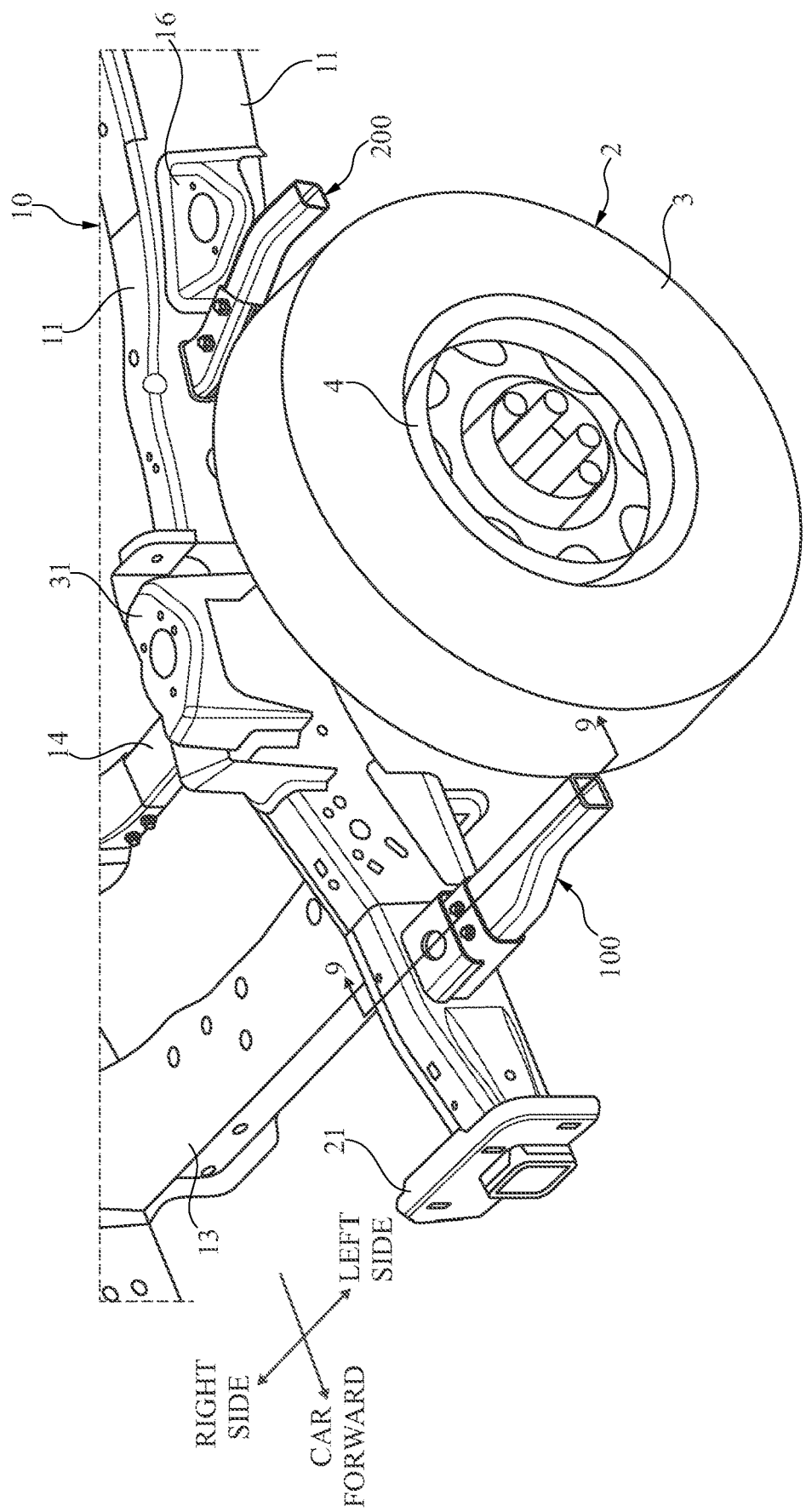
FIG. 5 is a partial, perspective graphic view of the exemplary embodiment of FIG. 3.

The vehicle frame 10 may further include left-side and right-side cab mount brackets 16 and 17, respectively, located proximal the second and third cross frame members 14 and 15, respectively, and coupled to the left-side and right-side side frame rails 11 and 12, respectively as best shown in FIG. 4. Each of the cab mount brackets 16 and 17 may include a passage or hole for receiving a post or other extension member of the cab 7 for coupling the cab 7 to the vehicle frame 10. The vehicle frame 10 may further include a pair of left-side and right-side shock tower brackets 31 and 32, respectively, located proximal the wheels 2 and between the first and second cross frame members 13 and 14, respectively, and coupled to the left-side and right-side side frame rails 11 and 12, respectively. The left-side and right-side shock tower brackets 31 and 32 may each include a passage or hole receiving a poster other extension member of the cab 7 for coupling the cab 7 to the vehicle frame 10. The vehicle frame 10 may further include left-side and right-side front impact absorber or bumper mount brackets 21 and 22, respectively, coupled to the car forward ends of the left-side and right-side side frame rails 11 and 12, respectively. The vehicle frame 10 and its various components may be preferably made from a high strength and/or ultra-high strength steel and may be coupled together using known or appropriate fastening or coupling structure or process, including in particular a metal inert gas (MIG) welding process.

Figure 1:
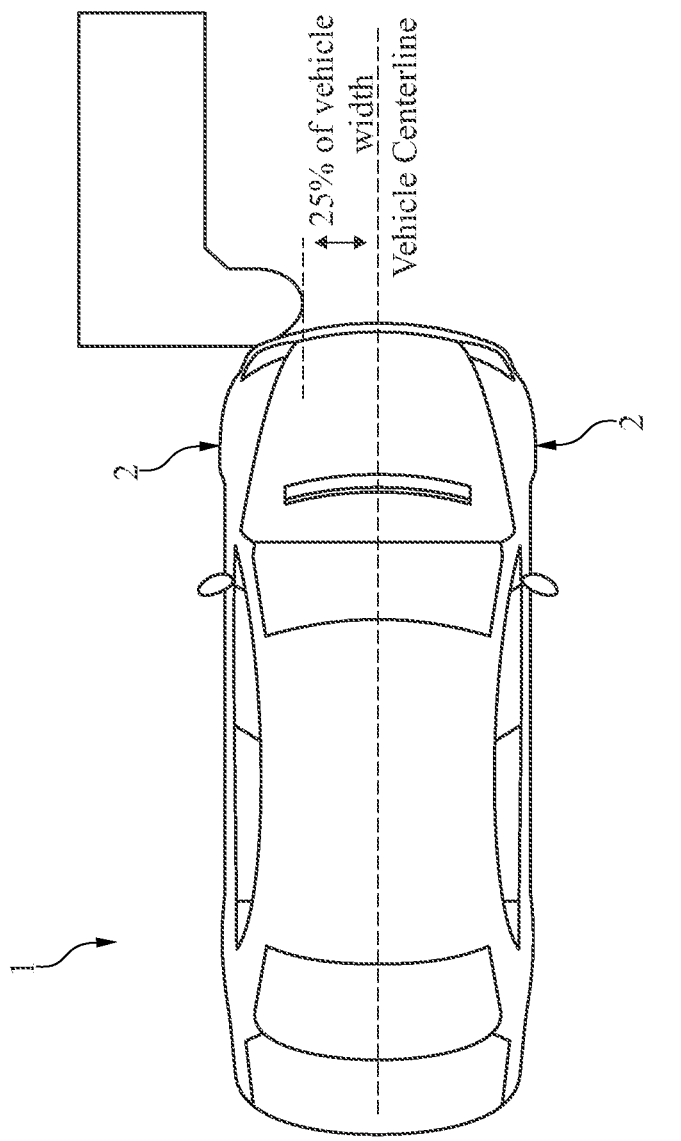
FIG. 1 is an overhead graphic view of a small overlap frontal crash test simulation including a vehicle.

The vehicle frame 10 may further include left-side and right-side front blocker structures 100 and left-side and right-side rear blocker structures 200 coupled to the left side and right side frame members 11 and 12, respectively. The front blocker structure 100 is coupled to the side frame rail 11 at a location car forward and proximal the wheel 2. The left side vehicle frame rail 11 includes a first hole or passage 41 and the left side wall of the frame rail 11 includes a second hole or passage 51 in the right side wall of the frame 11. The front blocker structure 100 is located in and extends through the first passage 41 and the second passage 51. The front blocker structure 100 extends in a direction substantially aligned with the cross car direction (which is normal or perpendicular to the car forward direction) and outward from the frame rail 11 such that in a small offset frontal impact (where the impact is less than 25% of the vehicle width (see FIG. 1)), the front blocker structure 100 will be impacted before the wheel 2. Since the front blocker structure 100 is coupled to the left side vehicle frame rail 11, at least a portion of the energy of the small offset impact will be transferred to the left side frame rail 11 and therefore not transferred to the wheel 2. Since there is less energy transferred to the wheel 2, there will be less energy to move the wheel 2 toward the cab 6 of the vehicle 1 and therefore there will necessarily be less intrusion of the occupant compartment 5. Accordingly, it may be appreciated that the front blocker structure 100 may function to limit, and to control and guide the movement of the wheel 2 during an offset impact to the vehicle 1.

Figure 6:
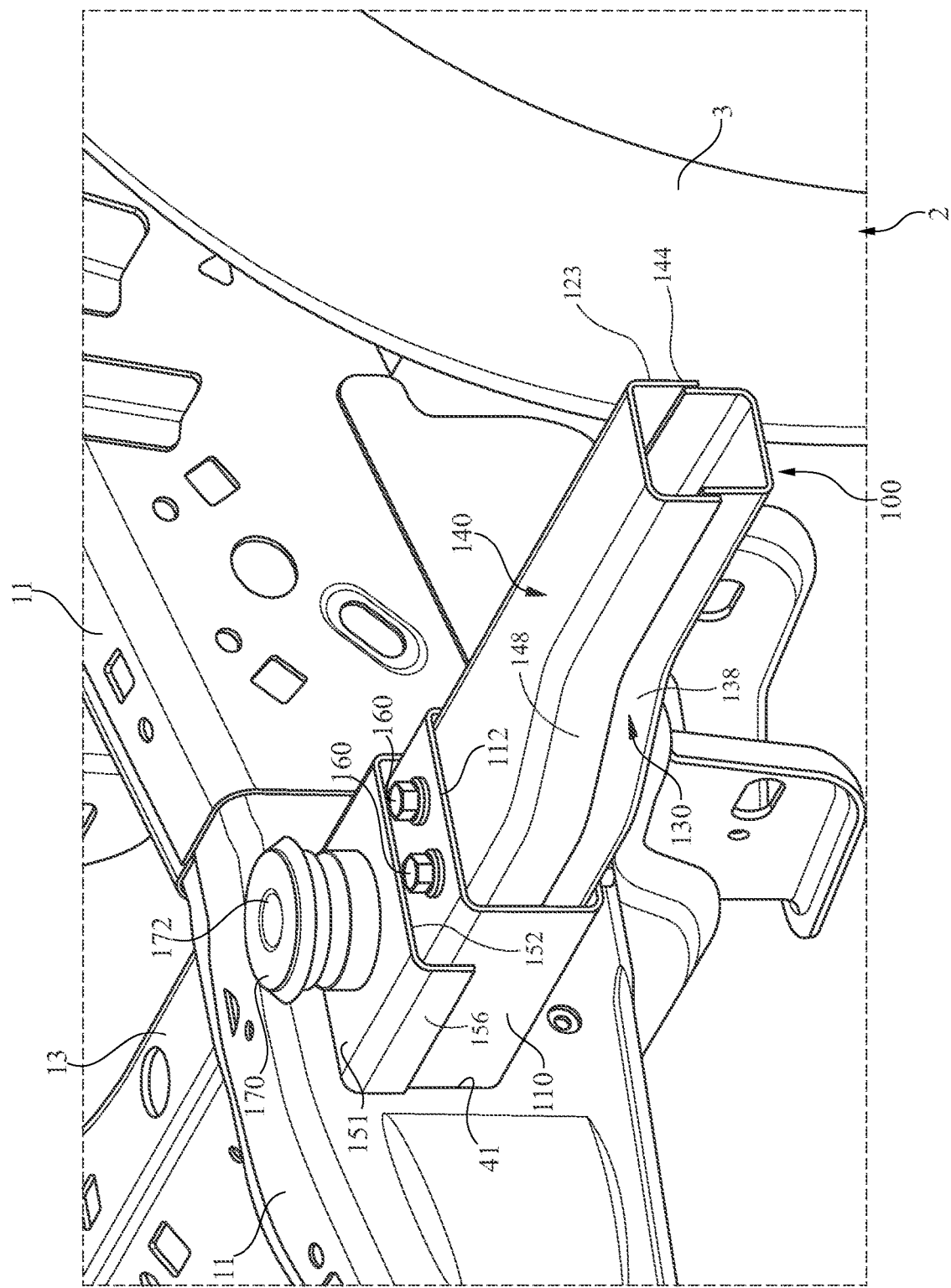
FIG. 6 is a partial, perspective graphic view of the front blocker structure according to the exemplary embodiment of FIG. 3.
Figure 7:
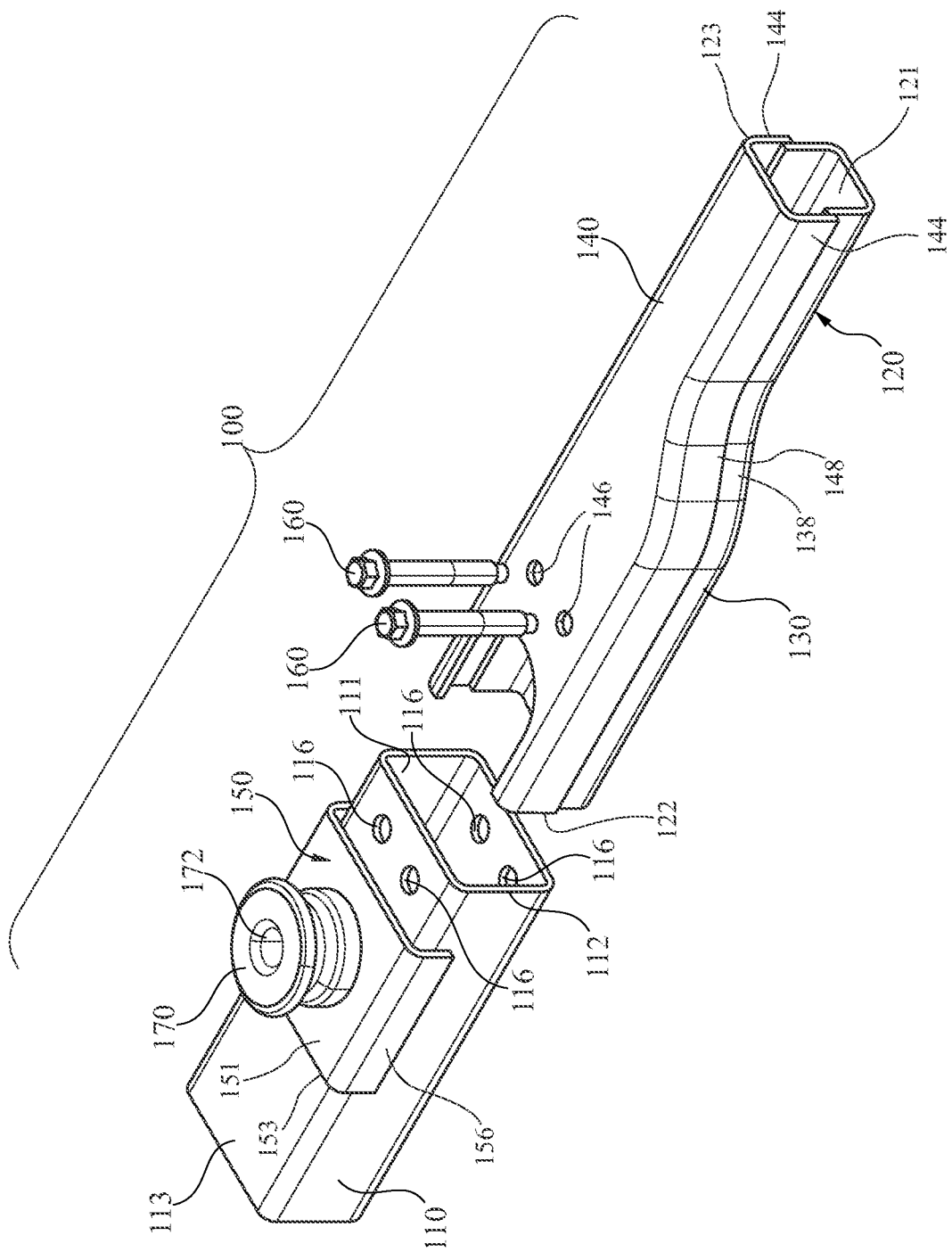
FIG. 7 is a partially exploded, perspective view detailing the components of the front blocker structure of FIG. 6.
Figure 8:
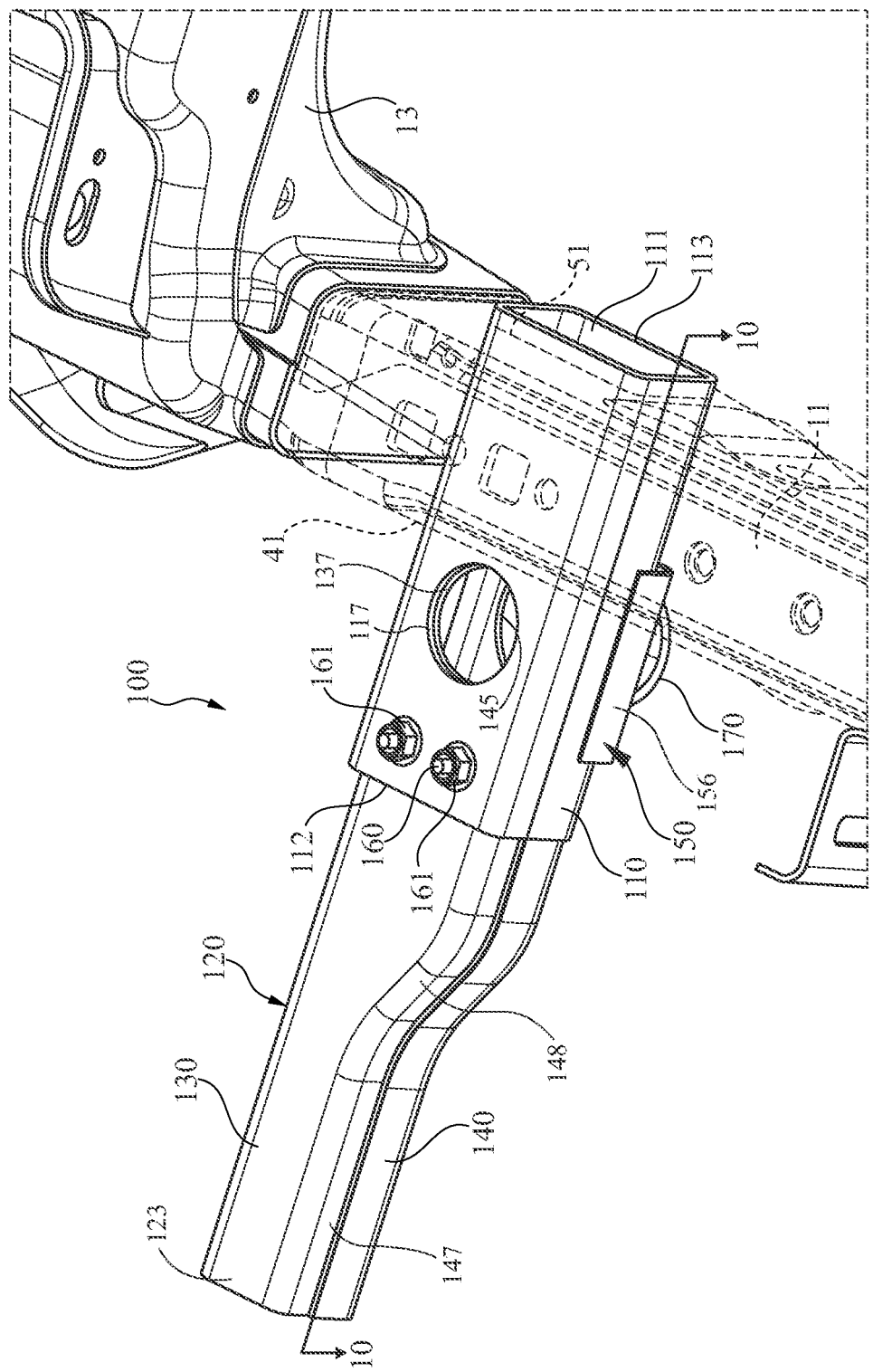
FIG. 8 is an alternate partial, perspective graphic view of the exemplary embodiment of FIG. 6 detailing the integration of the front blocker structure with the side frame rail of the vehicle frame.
Figure 9:
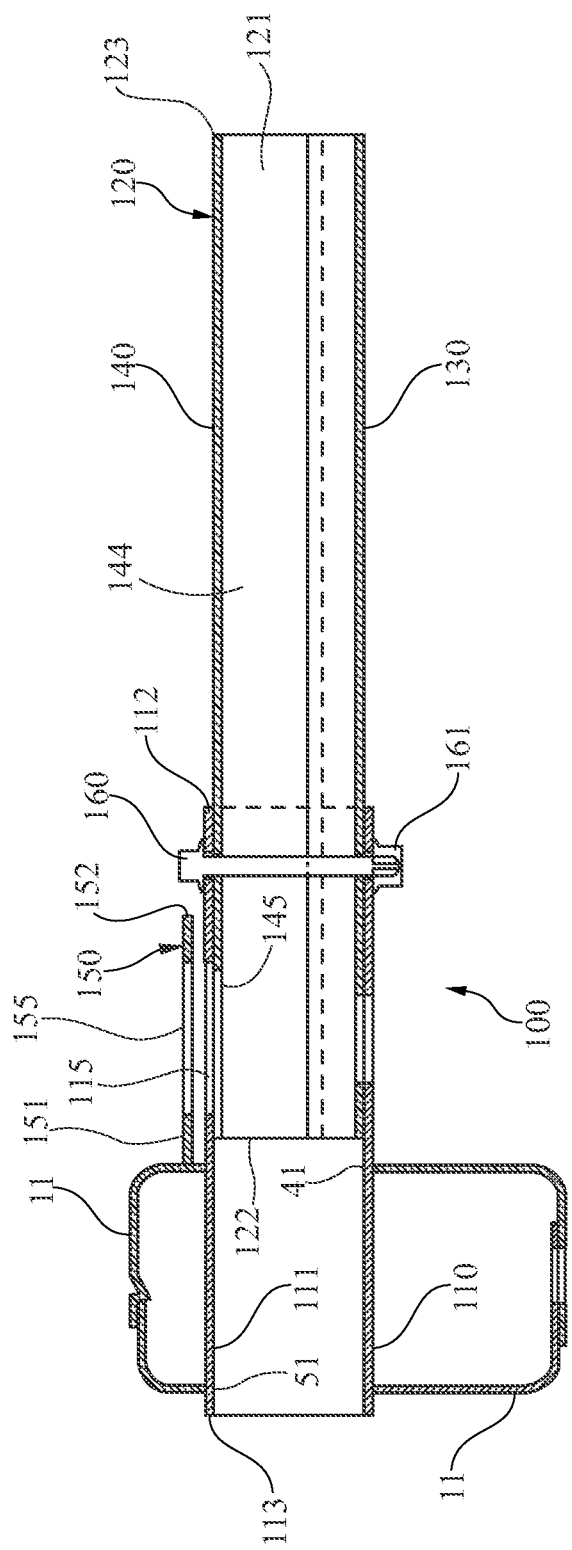
FIG. 9 is a graphic section view of the exemplary embodiment of the blocker structure of FIG. 5 taken along the line 9-9 shown therein.
Figure 10:
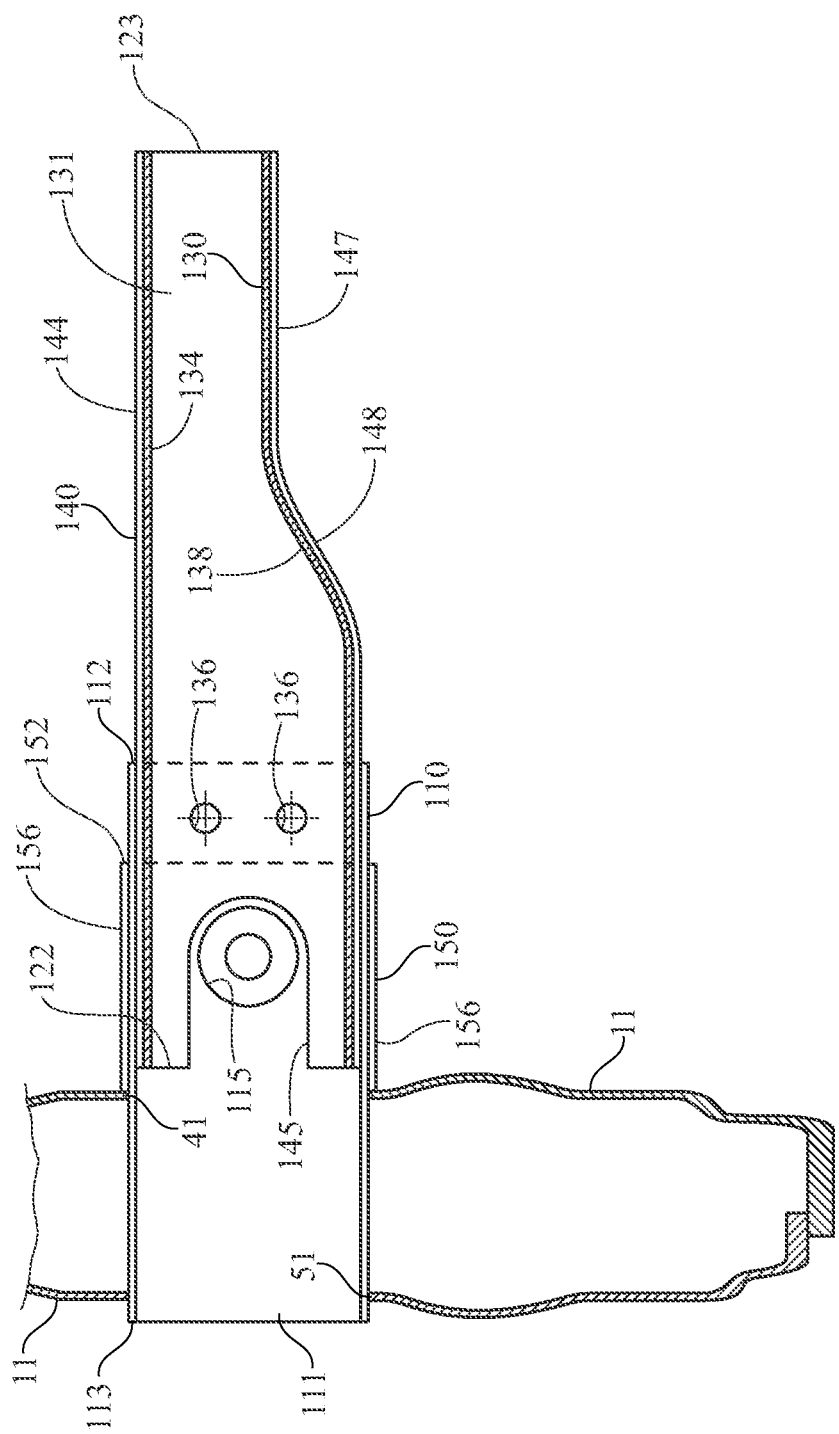
FIG. 10 is a partial, graphic section view of the exemplary embodiment of the blocker structure of FIG. 8 taken along the line 10-10 shown therein.

Referring more particularly known to FIGS. 7 through 10, the details of the front blocker structure 100 are shown. In particular, the front blocker structure 100 includes a base member 110 and an extension member 120. The front blocker structure 100 may also include, in one particular exemplary embodiment, a cab mount bracket or base member 150 coupled to the base member 110. The cab mount bracket 150 may preferably be a stamped high strength or ultrahigh strength steel material that includes a generally planar middle portion 151 and depending or folded legs 156. The middle portion 151 and the legs 156 may preferably be sized to correlate with the outer perimeter of the base member 110. The mounting bracket 150 includes a first end 152 and a second end 153 as best shown in FIGS. 6 and 7. The mounting bracket 150 may further include an opening, hole or passage 155 in the planar middle portion 151. The hole 155 may preferably be aligned with the hole 115 in the base member 110 and the passage 145 in the extension member 120 as best shown in FIG. 9. In one exemplary embodiment according to the present disclosure, the distal ends of the legs 156 may be welded to the outer periphery of the base member 110 using a MIG welding process.

In one particular exemplary embodiment, the base member 110 of the front blocker structure 100 may be a generally tubular structure made from a high strength or ultrahigh strength steel using a stamping, forming and welding process or any other known and appropriate process for producing an object from such material. The base member 110 includes a first end 112 and a second end 113 and has a generally longitudinal extent there between defining a generally longitudinal axis. The base member 110 has a generally rectangularly shaped cross-section in a direction perpendicular to the longitudinal axis but may have other known and appropriate cross-section shapes. The base member 110 has a generally tubular shape including a cavity, chamber or passage 111 extending from the first end 112 to the second end 113. The base member 110 further includes a plurality of holes or passages 116 in its upper and lower surfaces and located proximal the end 112. The base member 110 is coupled by welding to the left side frame rail 11, as best shown in FIGS. 8 and 9.

The base member 110 of the front blocker structure 100 is welded to the holes 41 and 51 in the left side frame rail 11. The end 113 of the base member 110 may extend inboard of the left side frame rail 11 in the cross car direction a sufficient amount such that a MIG weld may be formed around the entire perimeter of the base member 110 and the opening hole 51 of the left side frame rail 11. Similarly, a MIG weld may be formed around at least a portion of (or alternatively the perimeter of the base 110 and the opening hole 41 of the left side frame rail 11 to securely couple the base member 110 of the front blocker structure 100 to the vehicle frame 10. Alternatively the weld may be of any known or appropriate type and may be formed around the entire perimeter of the openings 41 and 51. The base member 110 further includes an opening or hole or passage 115 in the upper surface and located between the first end 112 and the second end 113. The base member 110 further includes an opening or hole or passage 117 in the lower surface and located between the first end 112 and the second end 113 and the hole 117 is generally aligned and overlapping with the hole 115 to provide the ability for a structure (such as a mounting post of the cab 6) and assembly tools to pass through the components of the base member 110.

The front blocker structure 100 may further include the extension member 120 which may be coupled to the base member 110. In one particular exemplary embodiment according to the present disclosure, the extension member 120 may include a first or bottom portion 130 and a second or upper portion 140 as best shown in FIGS. 7 through 10. The extension member 120 may be preferably coupled to the first end 112 of the base member 110 using any known or appropriate type of removable coupling, such as the fasteners 160. The extension member 120 has a generally longitudinal extent from a first end 122 to a second end 123. The extension member 120 has a generally tubular construction including a generally longitudinal axis and having a generally rectangularly shaped cross section in a direction perpendicular to the longitudinal axis of the extension member 120. Notably differing from the base member 110 which has a generally constant cross-section in a direction perpendicular to its longitudinal axis, the extension member 120 has a generally varying sized cross-section in a direction perpendicular to its longitudinal axis. The extension member 120 may have either a constant or a varied size cross-section (or a combination thereof) in a direction perpendicular to its longitudinal axis. Accordingly, the extension member 120 may include a generally hollow passage or chamber 121 extending from the first end 122 to the second end 123. The outer perimeter of the first end 122 of the extension member 120 may preferably be sized and shaped to be quickly and securely received in the passage 111 of the base member 110.

The first or bottom portion 130 of the extension member 120 may be formed from a high strength or ultrahigh strength steel in a stamping procedure to include a first surface 131 having a generally planar extent and including a pair of depending side extensions 134 and 137. The width of the first surface 131 varies between the first end 122 and the second end 123 of the bottom portion 130. The second or upper portion 140 of the extension member 120 may also be formed from a high strength or ultrahigh strength steel in a stamping procedure to include a first surface 141 having a generally planar extent and including a pair of depending side extensions 144 and 147 having complementary shapes to the depending side extensions 134 and 137 of the bottom portion 130. Since the depending side portions 144 and 147 overlap with at least a portion of the depending side extensions 134 and 137 of the bottom portion 130, the first surface 131 of the bottom portion 130 generally has the matching shape to the first surface 141 of the upper portion 140 but may be slightly larger. Accordingly, the extension member 120 may be assembled by producing the bottom portion 130, the top portion 140 and coupling the portions together and then welding them using a MIG welding or similar process.

In one exemplary embodiment according to the present disclosure, the first surface 141 of the upper portion 140 may include a passage or opening 145 extending from the first end 122 and toward the second end 123. The opening 145 in the upper surface 141 of the upper or top portion 140 of the extension member 120 overlaps with at least a portion of the openings 115 and 117 in the upper and lower surfaces, respectively, of the base member 110. Accordingly, as may be best seen in FIG. 9, the mounting post eight of the cab 7 is may extend through openings in the base member 110 and the extension member 120 so the cab 7 may be secured to the vehicle frame 10.

In one exemplary embodiment according to the present disclosure, the first surface 141 of the upper portion 140 may include holes 146 to be aligned with the holes 116 of the base member 110 when the first end 122 of the extension member 120 is received in the passage 111. Similarly, the first surface 131 of the bottom portion 130 may include holes 136 to be aligned with the holes 116 of the base member 110 and the holes 146 of the upper portion 140 when the first end 122 of the extension member 120 is received in the passage 111 of the base member 110. Accordingly, the extension member 120 may be coupled to the base member 110 using fasteners 160 which may be secured using nuts 161 which may be MIG or projection welded to the outer surface of the base member 110 once the fasteners 160 are inserted through the holes 146, 116 and 136 of the respective components and the nuts 161 are tightened. Accordingly, the design and construction of the front blocker structure 100 according to the present disclosure provides a bolt on extension member 120 to the base member 110 that may allow for more flexible assembly options.

In one exemplary embodiment according to the present disclosure, the front blocker structure 100 may further include a cab mounting pad, support, member or structure 170 coupled to the cab mount bracket 150. The cab mounting support 170 may include a passage 172 extending through the cab mounting support 170 and aligned with the hole 155 of the cab mounting bracket 150. The cab mounting support 170 may include any known or appropriate material and may preferably be made from an appropriately resilient yet sufficiently strong material for securely mounting the cab 6 to the vehicle frame 10 while also helping to properly insulate the occupant compartment 5 of the cab 6 from forces transferred form the vehicle frame 10.

In one particular exemplary embodiment according to the present disclosure, the extension member 120 may be coupled to the base member 110 at any appropriate time during the vehicle assembly process. In one exemplary embodiment, the extension member 120 may be coupled or assembled to the base member 110 during the manufacturing and assembly of the vehicle frame 10. In one particular exemplary embodiment according to the present disclosure, the extension member 120 may be separately produced from the production of the vehicle frame 10 and assembled to the vehicle frame 10 at any time prior to the cab 6 being assembled to the vehicle frame 10. More particularly, the extension member 120 may be assembled to the vehicle frame 10 after the vehicle frame 10 has been produced and transported to the vehicle assembly plant where the cab 6 may be assembled to the vehicle frame 10.

In one exemplary embodiment according to the present disclosure, the production of the vehicle frame 10 and the assembly of the vehicle 1 may include the process step of assembling the extension member 120 of the front blocker structure 100 to the base member 110 after the vehicle frame 10 has been transported to the assembly plant form the vehicle frame product plant or location. As indicated, the extension member 120 is coupled to the base member 110 using fasteners 160. In this manufacturing scenario, it is possible to produce the vehicle frames 10 including the base members 110 welded to the side frame rails 11 and 12 in a first vehicle frame manufacturing or production location and then ship the vehicle frames 10 to another location such as a vehicle assembly plant. The vehicle frames 10 may be stacked vertically and then the stacks of vehicle frames 10 may be loaded on a rail car or other carrier for shipping between locations. To reduce the costs of shipping it is desirable to have the stacks of vehicle frames 10 located as closely as possible together. In this particular exemplary embodiment, it should be appreciated that since vehicle frame 10 is shipped without the extension member 120 coupled to the base member 110 there will be no loss in the shipping density of the stacks of vehicle frames 10 on the rail car. Accordingly, in the present exemplary embodiment, the base members 110 are welded to the side frame members 11 and 12 during the assembly and production of the vehicle frame 10 and the base members 110 are sized such that the first end 112 of the base member 110 extends outboard of the side frame members 11 and 12 only a limited distance such that multiple vehicle frames 10 may be stacked for shipping to the vehicle assembly plant without any loss to the stacking density of the stacks of vehicle frames 10 as compared to the stacking density of the stacks of vehicle frames before the inclusion of the front blocker structure 100 according to the present disclosure. The same principles may also be applied to the other blocker structures of the exemplary embodiments of the present disclosure.

In one alternate exemplary embodiment according to the present disclosure, it may be noted that it is possible for both the base member 110 and the extension member 120 to be assembled to the vehicle frame 10 at the vehicle assembly plant after the vehicle frames 10 have been shipped to the vehicle assembly plant without any loss in the stacking density of the vehicle frames 10. In one alternate exemplary embodiment, the vehicle frame 10 may be produced with the multiple openings 41 and 51 in the side frame rails 11 and 12 and then the base members 110 may be coupled to the side frame rails 11 and 12 at the vehicle assembly plant. This alternate construction and method of production for the front blocker structure 100 has particular utility when a one-piece front blocker structure may be desired.

Figure 11:
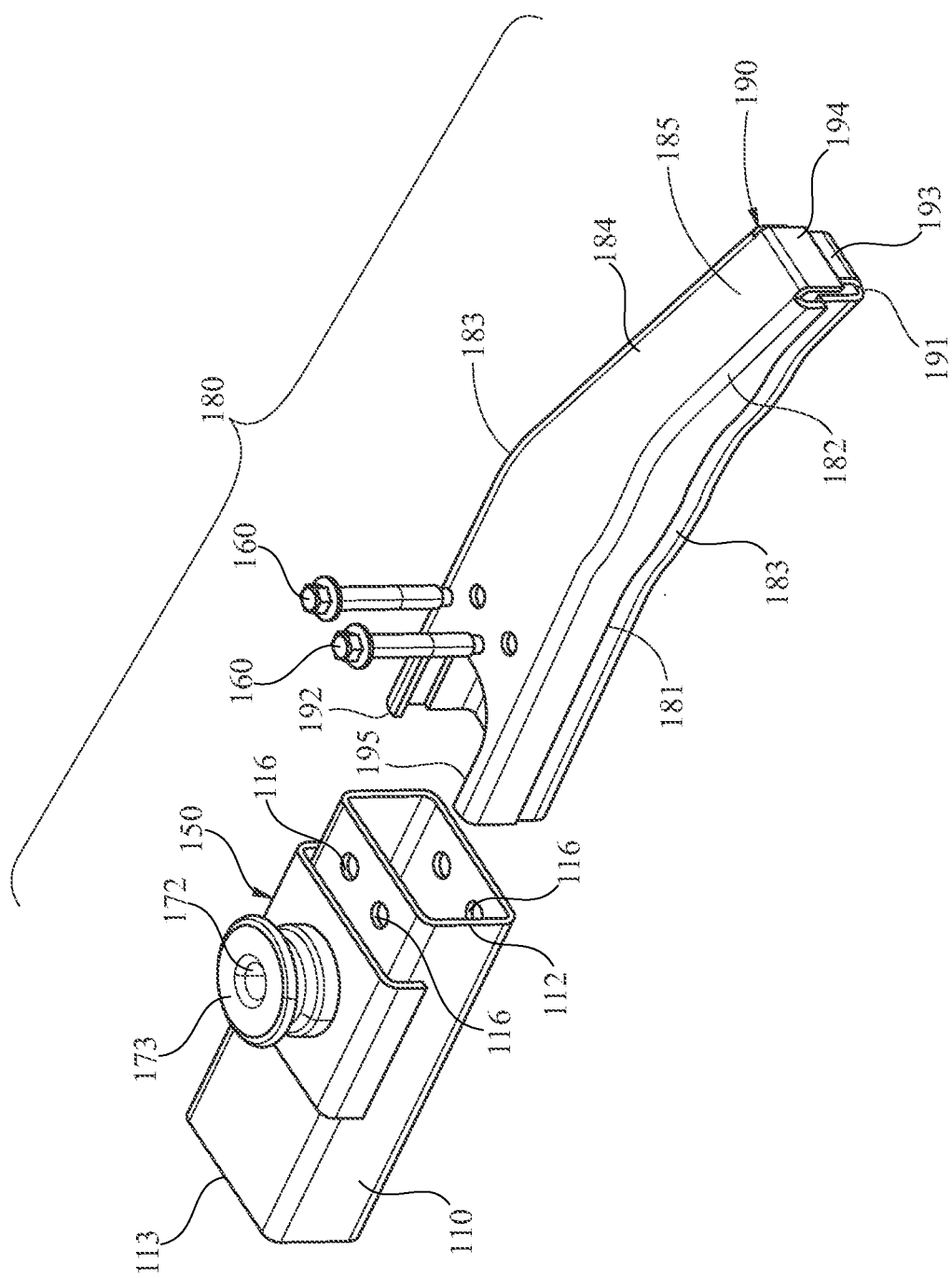
FIG. 11 is a partially exploded, perspective view detailing the components of a front blocker structure of an exemplary embodiment of the present disclosure.
Figure 13:
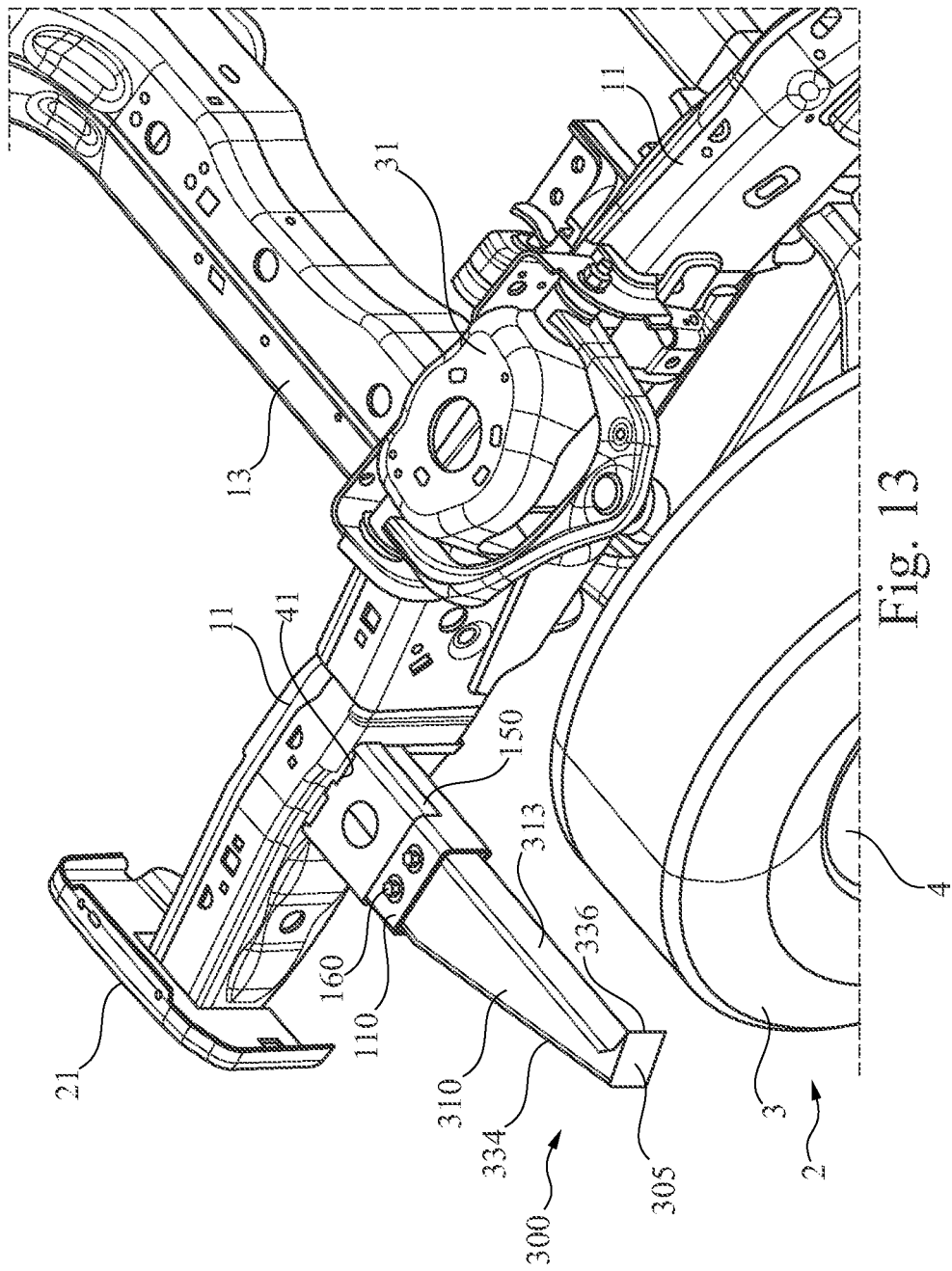
FIG. 13 is a partial, perspective graphic view of a front blocker structure including a tire deflation device according to an exemplary embodiment of the present disclosure.

Referring now in particular to the alternate exemplary embodiment of the present disclosure of FIGS. 2 and 11, there is disclosed a front blocker structure 180. The front blocker structure 180 may generally be similar in overall construction and application as the front blocker structure 100. The front blocker structure 180 may include a base member 110, a cab mounting bracket 150 and a cab support mount 170 that are generally the same as the front blocker structure 100. The front blocker structure 180 may include an extension member 190 having a unique construction as compared to the extension member 120 of the blocker structure 100.

The extension member 190 has a generally rectangular design and generally extends longitudinally and includes a longitudinal axis. The extension member 190 may include a first end 192 including an opening or passage 195 extending distally from the end 192 in a manner similar to the opening 145 in the end 122 of the extension member 120. The extension member 190 may further include holes 196 located distally from the end of the opening 195. The holes 196 may be distally located to be aligned with the holes 116 of the base member 110 when the end 192 of the extension member 190 is received in the passage 111 of the base member 110. The holes 196 may be located and sized appropriately to receive the fasteners 160 for coupling, or bolting on, the extension member 190 to the base member 110. The extension member 190 may include a car forward side 188 including an angle 182 from which an angled portion 185 extends and a car rearward side 189 including an angle 183 from which the angled portion 185 extends toward the end 191. The end 191 of the extension member 190 includes a lower portion 193 which is folded from the bottom surface of the extension member 190 and extends upward and an upper portion 194 which is folded from the top surface of the extension member 190 and extends downward as best shown in FIG. 11. In one exemplary embodiment of the present disclosure, the extension member 190 may preferably be produced as a single piece of high strength or ultrahigh strength sheet metal that may be stamped, punched, folded and formed into the shaped extension member 190 and including a seam 181.

While the vehicle 1 of the present disclosure is shown as including both a front blocker structure 100 and a rear blocker structure 200, it should be understood that it is possible to include either and/or both of the blocker structures on the vehicle as may be desired or appropriate for managing the crash forces and movement of the tire 3 during the offset frontal impact to the vehicle 1 to limit intrusion into the passenger compartment 5. Generally, the rear blocker structure 200 may be designed and constructed in a manner similar to the front blocker structure 100. The rear blocker structure 200 may be coupled to the left-hand and right-hand side frame rail members 11 and 12, respectively, of the vehicle frame 10. The left-hand frame rail member 11 may again include the opening 41 in which and end of the rear blocker structure 200 may be inserted and passed through the left-hand frame rail member 11. The end of the rear blocker structure 200 may be coupled to the left-hand frame rail 11 using a MIG welding process. Referring now in particular to FIGS. 2 through 5 and 12, there is disclosed in more detail the rear blocker structure 200 according to an exemplary embodiment of the present disclosure.

The rear blocker structure 200 may include a base member 210 which is shown in phantom lines in FIG. 12 to better show the coupling of an extension member 230 of the blocker structure 200 to the base member 210. The base member 210 includes an end 212 and has a generally square cross-section tubular shape including an opening or passage 211 extending between the ends of the base member 210. The base member 210 extends longitudinally and may include a bend or angle 205 along its longitudinal axis. The bend 205 is located outboard of the side of the left-hand frame rail 11 and aligns the end 212 of the base member and therefore the extension member 230 in a direction to avoid interfering with the envelope of the wheel 2 defined by the movement of the wheel 2 during normal operation of the vehicle 1. The extension member 230 may be a generally rectangular or square cross-section tubular shaped member including a passage extending from a first end 231 to a second end 232 which is inserted in the passage 211 of the base member 210. The extension member 230 may generally have any shaped cross-section appropriate for the noted application. The extension member 230 may have a generally longitudinal extent including a longitudinal axis. The extension member 230 includes a first portion 233 including a first portion of the longitudinal axis and a second portion 234 including a second portion of longitudinal axis. The first portion 233 is angularly offset from the second portion 234 by a bend 235. Accordingly, the longitudinal axis of the first portion 233 is also angularly offset from the longitudinal axis of the second portion 234. The sizes and angles of the first and second portions 233 and 234, respectively, and the bend to 35 are selected to locate the second blocker structure 200 proximal the envelope of the wheel 2 so that the second blocker structure 200 is only engaged by the wheel 2 due to an impact to the vehicle 1 causing the wheel 2 to be moved toward and engage the rear blocker structure 200 which, being coupled unanchored in the frame rail 11, limits the movement of the wheel 2 toward the passenger compartment 5 of the cab 6.

The base member 210 and the extension member 230 each include holes (not shown) for receiving the bolts are or fasteners 260 for coupling or bolting on the extension member 230 to the base member 210. Similar to the front blocker structure 100, the bolt on feature and structure of the rear blocker structure 200 allows the extension number member 230 to be coupled to the base member 210 at the vehicle assembly plant and therefore allows for the continued use of the existing vehicle frame 10 transportation resources and maintaining the existing vehicle frame 10 shipping density. The use of the bolt on extension member 230 to the base member 210 further allows for continued use of the suspension alignment units and the existing frame and pedestal lines in the vehicle assembly plant. The rear blocker 200 may include the bolt on the clip 240 located in the passage 211 of the base member 210 as best shown in FIGS. 12 and 12A.

The clip or support member 240 may be a generally planar sheet metal piece of material including a first formed end 241 and a second formed end 242 separated by a middle or bight portion 243. The ends 241 and 242 of the clip support 240 are formed to include generally circular or round-shaped passages 245 and 246, respectively, for providing a passage between the hole in the upper surface of the base member 210 and the hole in the lower surface of the base member 210 so that the shank of the fastener 260 may be easily and accurately passed through the passage 211 of the base member 210. In particular, the clip support 240 may be located in the passage 211 of the base member 210 and extend substantially between the upper surface and the lower surface of the passage 211 and may be welded in place using any known or appropriate weld type or process. The clip support 240 may provide additional support to the tubular structures of the base member 210 and the extension member 230 to allow the fasteners 260 to be torqued sufficiently tight without impairment to the members 210 and 230, respectively, and their connection. It is contemplated that the clip support 240 may be used with any of the blocker structures 100, 180, 200 and 300 of the present disclosure.

The bolt on front and rear blocker structures 100 and 200 respectively provide many advantages including the ability to design and implement a more optimal and tunable design by providing ability to select different material thicknesses for the base members 110 and 210 from the extension members 120 and 230, respectively.

Figure 14:
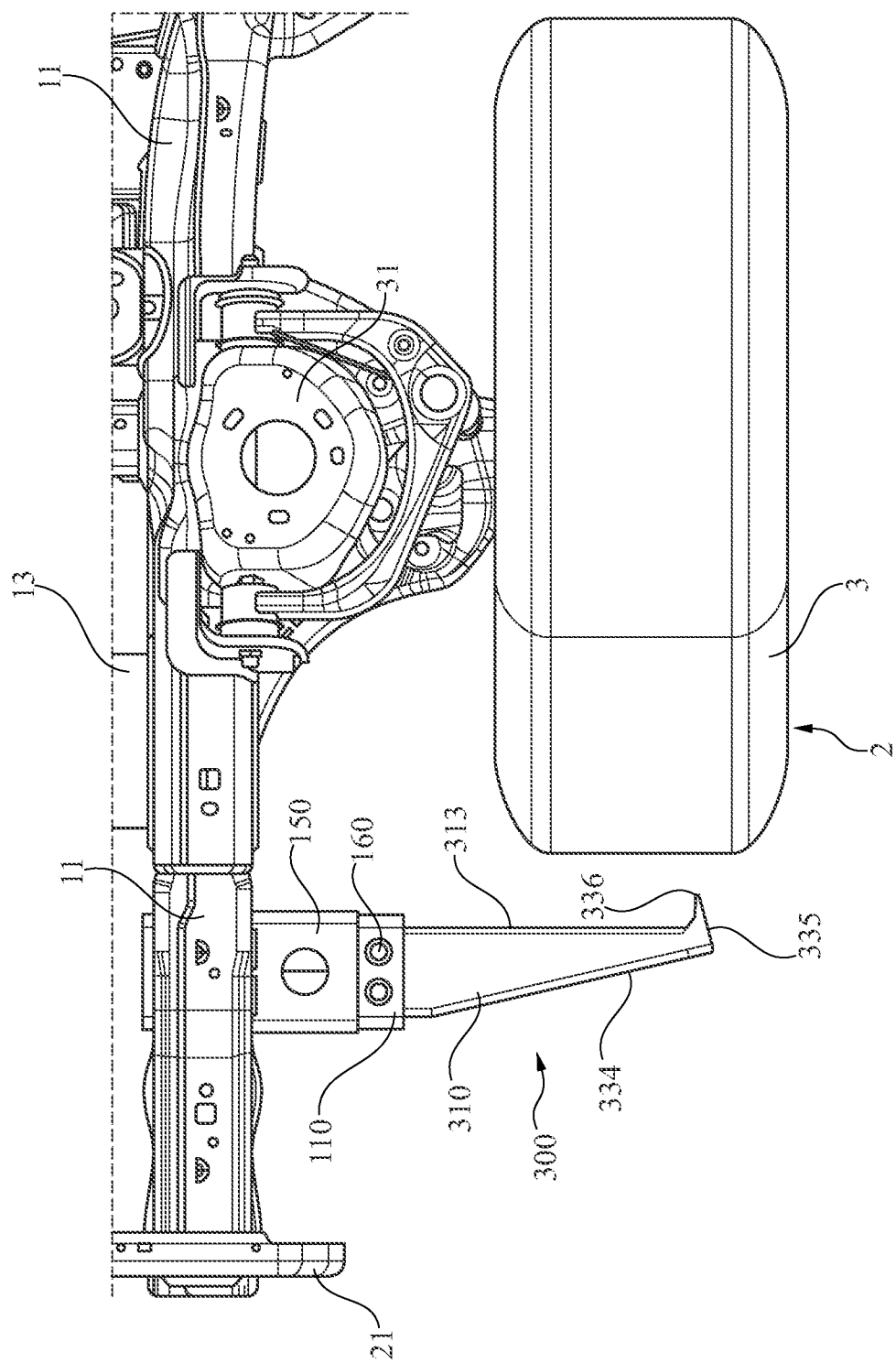
FIG. 14 is a top plan graphic view of the exemplary embodiment of FIG. 13.
Figure 15:
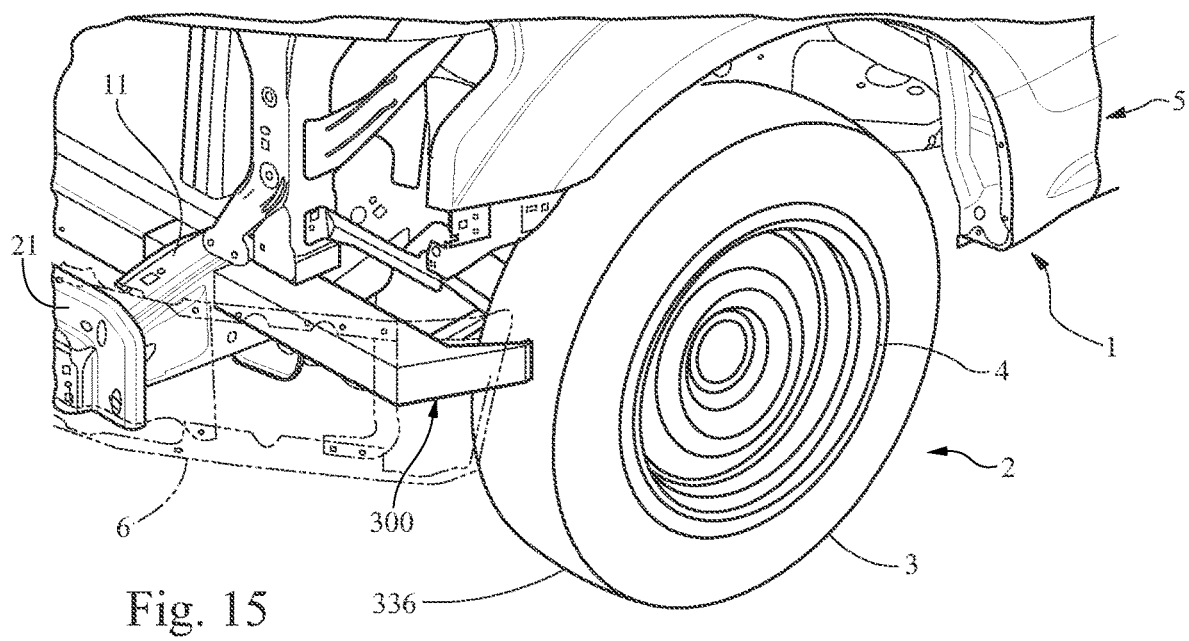
FIG. 15 is a partial, perspective graphic view of the exemplary embodiment of FIG. 13 prior to impact with the barrier of the test set up of FIG. 1.
Figure 16:
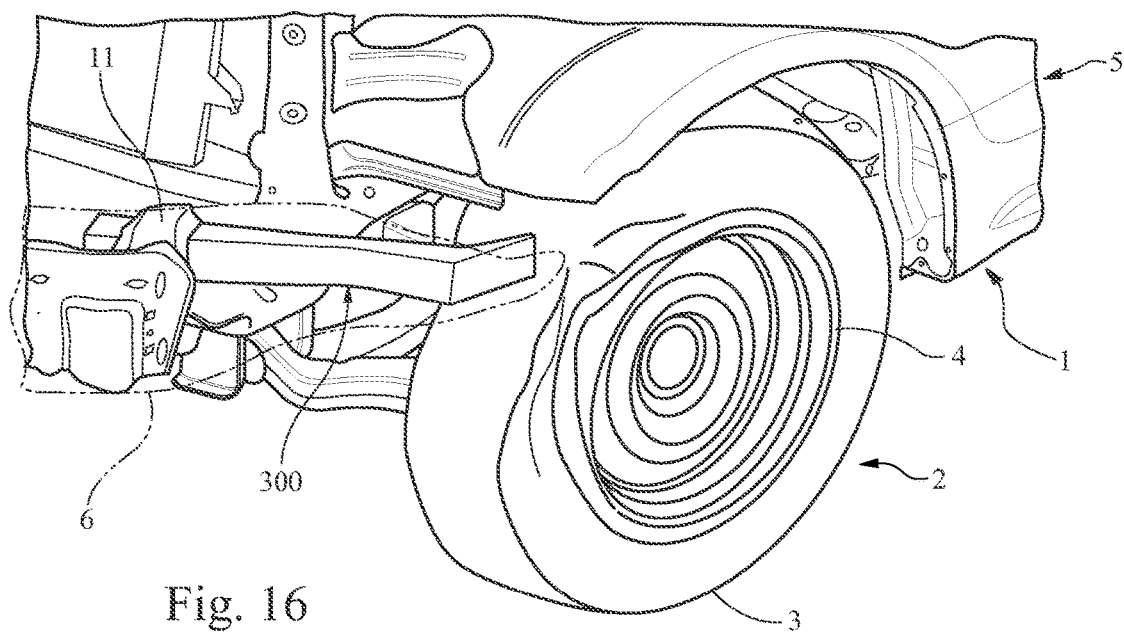
FIG. 16 is a partial, perspective graphic view of the exemplary embodiment of FIG. 13 after impact of the vehicle with the barrier of the test set up of FIG. 1.

In one exemplary embodiment of the present disclosure as best shown in FIGS. 13 through 16, there is disclosed a blocker structure 300 including a tire puncture or deflation device 310. The tire deflation device 310 of the blocker structure 300 may cause the tire 3 of the wheel 2 to deflate during an offset frontal impact thereby reducing the amount of mass and structure of the wheel 2 moving toward the passenger compartment 5 of the vehicle cab 6. Referring in particular to FIG. 14, the blocker structure 300 includes an extension member 310 having a car rearward side 313 and a car forward side 334. The extension member 310 is a generally longitudinal structure including a first end bolted onto the base member 110 using the bolts are fasteners 160. The extension member 310 has a generally rectangular cross-section in a direction perpendicular or normal to its longitudinal axis. In particular, the side 334 is at an angle to the side 313 such that the cross-section becomes smaller or distal from the base member 110. The extension member 310 extends to an end 335 which includes a car rearward facing tire deflation device 336 in the form of a sharp or angled point or edge aligned in a direction intersecting the tire 3 of the wheel 2 such that an offset impact similar to that shown in FIG. 1 will cause the blocker members 300 to move toward the wheel 2. Once the blocker member 300 moves sufficiently toward the wheel 2, the tire deflation device 336 sufficiently engages the tire 3 rupturing its integrity and releasing the pressurized air or other fluid contained therein, as best shown in FIG. 16. The tire deflation device 336 is preferably designed sufficiently such that any body structure or other materials, such as those used to close out the internal vehicle structures and provide an appropriate outward finished appearance to the vehicle 1, located between the blocker member 300 and the tire 3 of the wheel 2 will not prevent the tire deflation device 336 from being effective during the offset frontal impact to the vehicle 1.

In one exemplary embodiment of the present disclosure it is understood that any of the features of the various blocker structures 100, 180, 200 and 300 may be used with any of the other blocker structures. In one specific example, it may be possible to use the extension member 120 of the blocker structure 100 and include a tire deflation device 310 therein. Additionally, it is expressly contemplated by the present disclosure that it may be possible for the tire deflation device 310 to be incorporated in the rear blocker structure 200 such that the tire 3 of the wheel 2 will not be deflated by the tire deflation device 310 until the frontal impact causes the front blocker structure 100 or 180 or 300 to move car rearward until it impacts the wheel 2 and moves it into engagement with the rear blocker structure 200. It is expressly contemplated by the present disclosure that any and all such combinations and substitutions of parts is possible. In another specific example, it is expressly contemplated that the clip 240 of the rear blocker structure 200 may be used for coupling any extension member to any base member. For example, the clip 240 may be welded in the passage 111 of the base member 110 for bolting on the extension member 120 using the bolts 160.

Any numerical values recited herein or in the figures are intended to include all values from the lower value to the upper value in increments of one unit provided that there is a separation of at least 2 units between any lower value and any higher value. As an example, if it is stated that the amount of a component or a value of a process variable such as, for example, temperature, pressure, time and the like is, for example, from 1 to 90, preferably from 20 to 80, more preferably from 30 to 70, it is intended that values such as 15 to 85, 22 to 68, 43 to 51, 30 to 32 etc. are expressly enumerated in this specification. For values which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner. As can be seen, the teaching of amounts expressed as "parts by weight" herein also contemplates the same ranges expressed in terms of percent by weight. Thus, an expression in the Detailed Description of the Invention of a range in terms of at "'x' parts by weight of the resulting polymeric blend composition" also contemplates a teaching of ranges of same recited amount of "x" in percent by weight of the resulting polymeric blend composition."

Unless expressly stated, all ranges are intended to include both endpoints and all numbers between the endpoints. The use of "about" or "approximately" in connection with a range applies to both ends of the range. Thus, "about 20 to 30" is intended to cover "about 20 to about 30", inclusive of at least the specified endpoints.

The use of the term "consisting essentially of" to describe a combination shall include the elements, ingredients, components or steps identified, and such other elements ingredients, components or steps that do not materially affect the basic and novel characteristics of the combination. The use of the terms "comprising" or "including" to describe combinations of elements, ingredients, components or steps herein also contemplates embodiments that consist essentially of the elements, ingredients, components or steps. By use of the term "may" herein, it is intended that any described attributes that "may" be included are optional.

The disclosure of "a" or "one" to describe an element, ingredient, component or step is not intended to foreclose additional elements, ingredients, components or steps. Plural elements, ingredients, components or steps can be provided by a single integrated element, ingredient, component or step. Alternatively, a single integrated element, ingredient, component or step might be divided into separate plural elements, ingredients, components or steps.

It is understood that the present description is intended to be illustrative and not restrictive. Many embodiments as well as many applications besides the examples provided will be apparent to those of skill in the art upon understanding the present disclosure. The scope of the claimed invention should, therefore, not be determined with limiting reference to the description, but should instead be determined with reference to the appended claims, along with the full scope of equivalents to which such claims are entitled. Any disclosure of an article or reference, including patent applications and publications, is incorporated by reference herein for all purposes. Any omission in the following claims of any aspect of subject matter disclosed herein is not a disclaimer of such subject matter.

The invention claimed is:

1. A vehicle comprising:
   a frame rail including an inboard side, an outboard side, and an opening extending through the inboard side and the outboard side;
   a shock tower bracket extending from the frame rail;
   a cab mount bracket positioned on the frame rail in a vehicle-rearward position relative to the shock tower bracket, the cab mount bracket extending outboard from the outboard side of the frame rail, the cab mount bracket being welded to the outboard side of the frame rail; and
   a blocker adjacent the cab mount bracket, the blocker positioned on the frame rail in a vehicle-rearward position relative to the shock tower bracket, and the blocker positioned on the frame rail in a vehicle-forward position relative to the cab mount bracket;
   the blocker extending into the opening and passing through the frame rail from the outboard side of the frame rail to the inboard side of the frame rail;
   the blocker is welded to the inboard side of the frame rail and the outboard side of the frame rail at the opening;
   the blocker extending outboard from the outboard side of the frame rail;
   the blocker is elongated outboard from the frame rail; and
   the blocker extends from the outboard side of the frame rail farther than the cab mount bracket extends from the outboard side of the frame rail.

2. The vehicle as set forth in claim 1, further comprising a cab mounted to the cab mount bracket in a body-on-frame construction.

3. The vehicle as set forth in claim 1, further comprising a front tire, the blocker being between the cab mount bracket and the front tire.

4. The vehicle as set forth in claim 3, wherein the blocker is behind a path traveled by the front tire during forward movement of the front tire.

5. The vehicle as set forth in claim 1, wherein the blocker is behind a path traveled by a front tire during forward movement of the front tire.

6. The vehicle as set forth in claim 1, wherein the blocker is cantilevered from outboard side of the frame rail.

7. The vehicle as set forth in claim 1, wherein the blocker includes a base member extending into the opening and welded to the frame rail.

8. The vehicle as set forth in claim 7, wherein the blocker includes an extension member fixed to the base member with a fastener, the extension extending outboard from the base member.

9. The vehicle as set forth in claim 1, wherein the frame rail is a left-side frame rail.

10. A vehicle comprising:
    a frame rail including an inboard side, an outboard side, and an opening extending through the inboard side and the outboard side;
    a shock tower bracket extending from the frame rail;
    a cab mount bracket positioned on the frame rail in a vehicle-rearward position relative to the shock tower bracket, the cab mount bracket extending outboard from the outboard side of the frame rail, the cab mount bracket being welded to the outboard side of the frame rail; and
    a blocker adjacent the cab mount bracket, the blocker positioned on the frame rail in a vehicle-rearward position relative to the shock tower bracket, and the blocker positioned on the frame rail in a vehicle-forward position relative to the cab mount bracket;
    the blocker extending into the opening and passing through the frame rail from the outboard side of the frame rail to the inboard side of the frame rail;
    the blocker is welded to the inboard side of the frame rail and the outboard side of the frame rail at the opening;
    the blocker extending outboard from the outboard side of the frame rail;
    the blocker is tubular and elongated outboard from the frame rail; and
    the blocker extends from the outboard side of the frame rail farther than the cab mount bracket extends from the outboard side of the frame rail.

11. The vehicle as set forth in claim 10, further comprising a cab mounted to the cab mount bracket in a body-on-frame construction.

12. The vehicle as set forth in claim 10, further comprising a front tire, the blocker being between the cab mount bracket and the front tire.

13. The vehicle as set forth in claim 12, wherein the blocker is behind a path traveled by the front tire during forward movement of the front tire.

14. The vehicle as set forth in claim 10, wherein the blocker is behind a path traveled by a front tire during forward movement of the front tire.

15. A vehicle comprising:
    a frame rail including an inboard side, an outboard side, and an opening extending through the inboard side and the outboard side, the frame rail being a left-side frame rail;
    a shock tower bracket extending from the frame rail;
    a cab mount bracket positioned on the frame rail in a vehicle-rearward position relative to the shock tower bracket, the cab mount bracket extending outboard from the outboard side of the frame rail, the cab mount bracket being welded to the outboard side of the frame rail;

a blocker adjacent the cab mount bracket, the blocker positioned on the frame rail in a vehicle-rearward position relative to the shock tower bracket, and the blocker positioned on the frame rail in a vehicle-forward position relative to the cab mount bracket;

the blocker extending into the opening and passing through the frame rail from the outboard side of the frame rail to the inboard side of the frame rail;

the blocker is welded to the inboard side of the frame rail and the outboard side of the frame rail at the opening;

the blocker extending outboard from the outboard side of the frame rail;

the blocker is tubular and elongated outboard from the frame rail; and the blocker extends from the outboard side of the frame rail farther than the cab mount bracket extends from the outboard side of the frame rail;

a cab mounted to the cab mount bracket in a body-on-frame construction;

a front tire, the blocker being between the cab mount bracket and the front tire.

16. The vehicle as set forth in claim 15, wherein the blocker is behind a path traveled by the front tire during forward movement of the front tire.

17. The vehicle as set forth in claim 15, wherein the blocker is cantilevered from outboard side of the frame rail.

18. The vehicle as set forth in claim 15, wherein the blocker includes a base member extending into the opening and welded to the frame rail.

19. The vehicle as set forth in claim 18, wherein the blocker includes an extension member fixed to the base member with a fastener, the extension extending outboard from the base member.

* * * * *